United States Patent [19]

Majlessi

[11] Patent Number: 4,842,583
[45] Date of Patent: Jun. 27, 1989

[54] COLONIC IRRIGATION TUBE

[76] Inventor: Heshmat Majlessi, 33 Cedar St., Rye, N.Y. 10580

[21] Appl. No.: 136,948

[22] Filed: Dec. 23, 1987

[51] Int. Cl.[4] .............................................. A61M 3/00
[52] U.S. Cl. ........................................ 604/43; 604/275
[58] Field of Search .................... 604/41, 43, 39, 272, 604/275, 332, 334, 173, 35, 40, 42, 45, 327, 325; 128/227

[56] References Cited

U.S. PATENT DOCUMENTS

| | | | |
|---|---|---|---|
| 565,386 | 8/1896 | Meengs | 604/41 |
| 669,910 | 3/1901 | Ball | 604/41 |
| 693,358 | 2/1902 | Westlake | 604/39 |
| 1,245,845 | 11/1917 | White | 604/41 |
| 1,758,332 | 5/1930 | Pitam et al. | 128/227 |
| 1,823,951 | 7/1931 | O'Neill | 604/39 |
| 2,148,541 | 2/1939 | Dierker | 604/35 |
| 2,257,072 | 9/1941 | Coombs | 604/35 |
| 3,394,705 | 7/1968 | Abramson | 604/43 |
| 3,421,510 | 1/1969 | Kettenbach | 604/45 |
| 3,593,713 | 7/1971 | Bogoff | 604/27 |
| 3,768,475 | 10/1973 | Osborne | 604/275 |
| 3,981,299 | 9/1976 | Murray | 604/43 |
| 4,117,847 | 10/1978 | Clayton | 604/328 |
| 4,419,099 | 12/1983 | Miller | 604/275 |
| 4,504,270 | 3/1985 | Miller | 604/275 |
| 4,637,814 | 1/1987 | Leiboff | 604/41 |

Primary Examiner—John D. Yasko
Attorney, Agent, or Firm—Lilling & Greenspan

[57] ABSTRACT

A colon irrigation device includes a tube flexible material with a second tube of smaller dimensions running along the inside surface of the larger external tube. Outlet apertures are provided for releasing irrigation fluid first through the inner tube or conduit, and inlet apertures are provided on the larger outer tube for receiving the irrigation fluid at a distal end of the colon. An enlarged end of the outer tube facilitates gripping of the tube once inserted into the colon so that it can be brought to the area to be irrigated. In the alternative, an inflatable bladder or balloon is provided which supplied with compressed air through a third tube running along the inside surface of the larger outer tube which can be inflated once the device is inserted into the colon and inflated to facilitate the gripping.

9 Claims, 2 Drawing Sheets

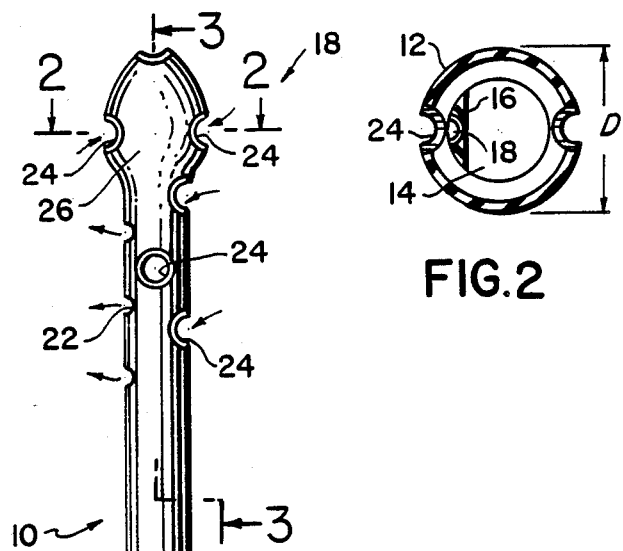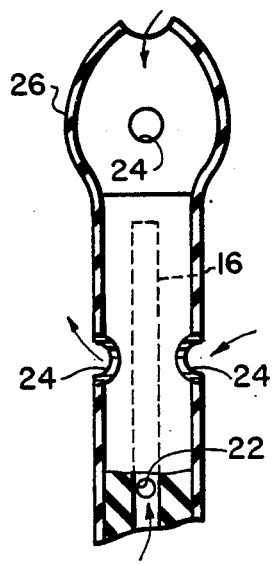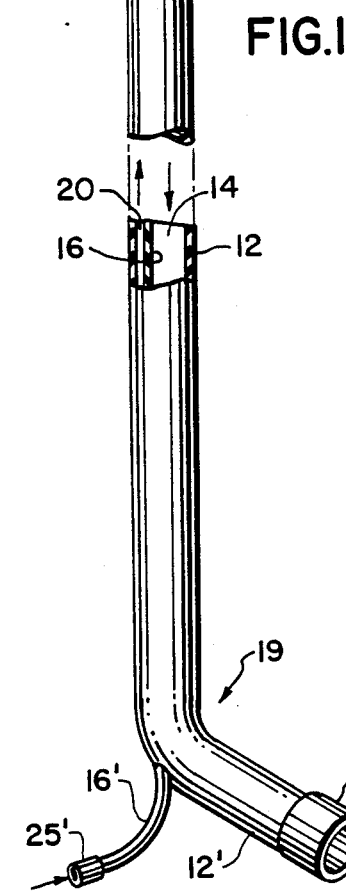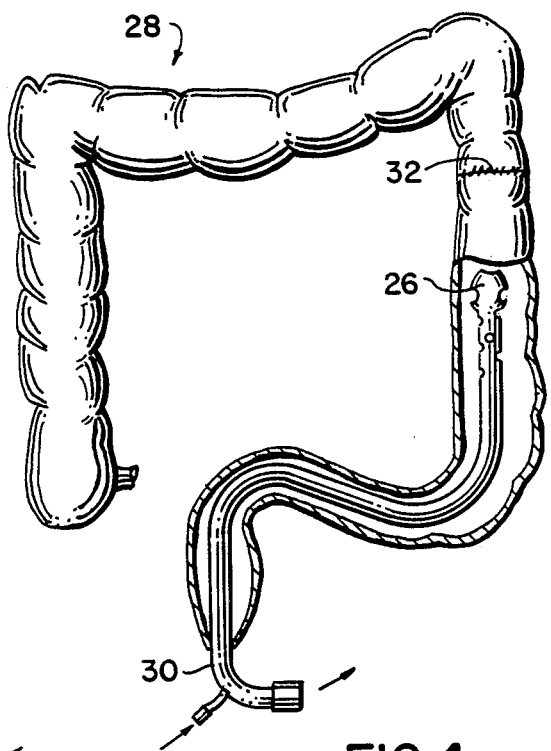

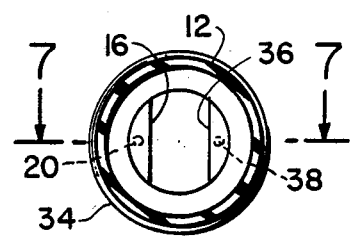
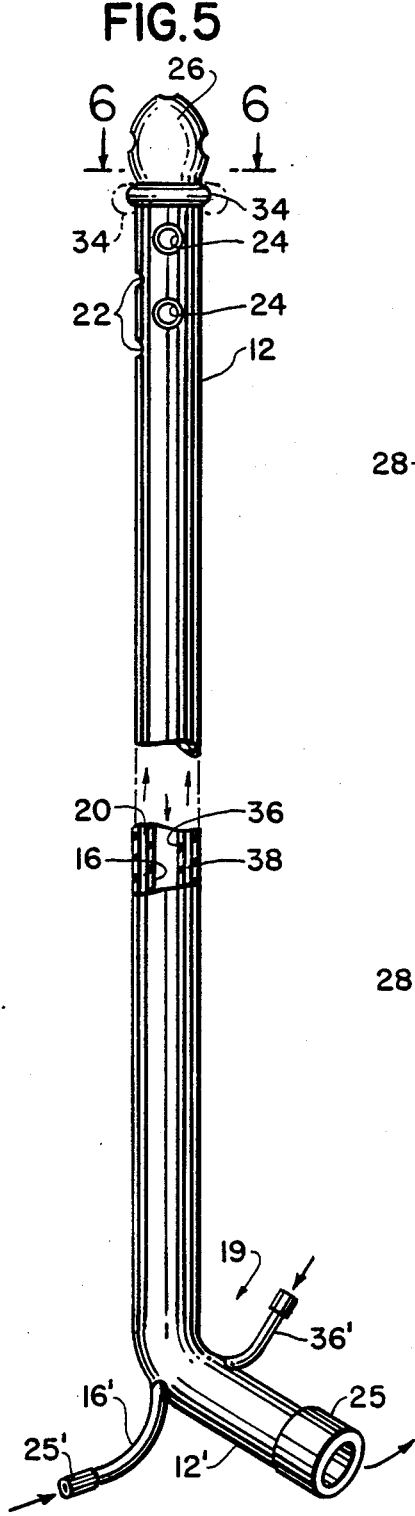
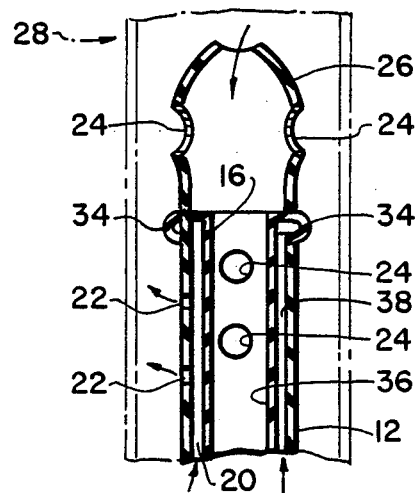
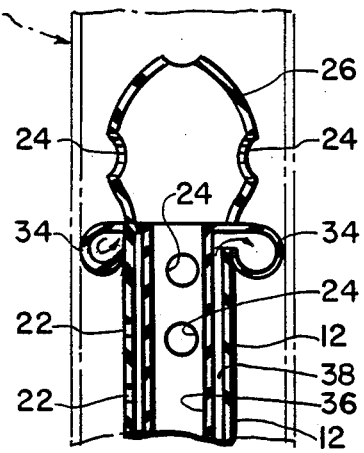

COLONIC IRRIGATION TUBE

BACKGROUND OF THE INVENTION

This invention relates to surgical implements and, more particularly, to a colonic irrigation tube for cleaning the colon prior to colonic anastomosis.

DESCRIPTION OF THE PRIOR ART

During intestinal surgery, it is important to irrigate at least the lower part of the colon or large intestine and remove fecal material to prepare for anastomosis or a re-section of the large intestine. Such surgery may become necessary to eliminate tumors, infections or bleeding. The irrigation of the colon, therefore, is important to facilitate such surgery as well as to prevent infection.

Numerous aspirating devices have been proposed. For example, in U.S. Pat. No. 4,642,092, issued to Moss, a gastrointestinal aspirating device is disclosed which is inserted into a patient's body and includes a number of lumens and orifices in such lumens for feeding and aspirating a material in the proximae segment of the small bowel. However, the device is intended to be inserted through the abdominal wall. A balloon is disposed on the device which enters the stomach and is inflated to sandwich the stomach wall between the balloon and the abdominal wall to anchor the device. However, this device is not intended for irrigating the colon, but to feed and aspirate the stomach and proximal segment of the small bowel following gastrointestinal surgery. Moss seeks to alleviate the normally deteriorated gastrointestinal functions and to aspirate air swallowed by the patient which further interferes with and complicates gastrointestinal functions. The Moss device is a post-operative device.

In U.S. Pat. No. 4,364,394, issued to Wilkinson, a combined sump drainage and irrigation device is disclosed which is specifically designed to be readily insertable through the abdominal wall into the peritoneal cavity in order to irrigate and drain and to allow for fluid injection facilitating the maintenance of sterility. The device, in the nature of an apertured tube structure including a plurality of lumens, is provided with an outer inflatable bladder which is intended to be positioned immediately inward of the incision and subsequently inflated as desired in order to prevent accidental withdrawal of the tube of structure from the body cavity.

A similar device is disclosed in U.S. Pat. No. 4,356,684, issued to Vazquez, which is intended to be used during the treatment following certain types of gastrointestinal surgery to aspirate and remove excess or undesirable gastric fluids and swallowed air. An intragastric balloon is provided which is initially deflated to facilitate surgical implantation into the stomach of the patient through the gastromic incision. Upon inflation, the balloon is selectively and positively positioned to prevent undesired or inadvertent removal, partial withdrawal or migration of the gastronomy tube from the stomach.

In U.S. Pat. No. 2,148,541 and 2,257,072, to Dierker and Coombs, respectively, colonic irrigators are disclosed which include relatively short tubes intended to be inserted through the rectum. However, these tubes cannot and are not intended to be moved proximate to the portion of the colon where the anastomosis is to take place and, therefore, irrigation is inefficient and less effective.

SUMMARY OF THE INVENTION

One of the objects of the present invention is to provide a colonic irrigation device which can be used to effectively and efficiently irrigate the colon and particularly that portion thereof where anastomosis is to take place. Another object of the present invention is to provide a colonic irrigation tube of the type under discussion which is simple to use.

It is still another object of the present invention to provide a colonic irrigation tube which can be used to irrigate any part of the colon or lower intestine.

It is yet another object of the present invention to provide a colonic irrigation tube which can be maintained in the colon following re-anastomosis to decompress the large intestine to eliminate the need for a nasal gastric tube and for aspirating gases and air swallowed by the patient.

It is still another object of the present invention to provide a colonic irrigation tube which permits rapid and efficient irrigation of the colon and, thereby, speeds up surgery and reduces the possibility of infection or complications due to compression of the large intestine.

In order to achieve the above objects as well as others which will become apparent hereafter, a colon irrigation device in accordance with the present invention comprises a tube made of a flexible material and defining, during use, a distal end received within a colon to be irrigated and an opposing proximal end which is maintained external of the colon, said tube further defining first and second conduit means extending between said proximal and distal ends, the proximal end of said first conduct means being adapted to be connected to a source of irrigation fluid and the proximal end of said second conduit means being adapted to be connected to a fluid evacuation system, said distal ends of said first and second conduit means being substantially closed and having outlet aperture means for discharging fluid from the distal end of said first conduit means into the colon and inlet aperture means for receiving the irrigating fluid at the distal end of said conduit means. Gripping means is provided at the distal end of said tube for allowing sensing and gripping of said distal end of said tube through the wall of the colon.

BRIEF DESCRIPTION OF THE DRAWINGS

Further advantages of the invention will become apparent from the following descriptions of preferred embodiments of the invention, taken in conjunction with the accompanying illustrative drawings, in which:

FIG. 1 is a side elevational view of the colonic irrigation tube in accordance with the present invention, partially in cross-section, showing the tube in its fully extended position, and illustrating the internal conduits or lumens for the feeding and aspirating of irrigation fluids;

FIG. 2 is an enlarged cross-sectional view of the tube shown in FIG. 1, taken along line 2—2;

FIG. 3 is an enlarged cross-sectional view of the tube shown in FIG. 1, taken along line 3—3;

FIG. 4 is a diagrammatic view of the colon or lower intestine, partially broken away, showing how the colonic irrigation tube in accordance with the present invention is intended to be used;

FIG. 5 is similar to FIG. 1, but showing another embodiment of the invention, including an additional conduit or lumen for the inflation of an inflatable bladder or balloon which replaces the enlarged end on the embodiment shown in FIG. 1;

FIG. 6 is an enlarged cross-sectional view of the tube shown in FIG. 5, taken along line 6—6;

FIG. 7 is a cross-sectional view of the tube shown in FIG. 6, taken along line 7—7, showing the balloon or inflatable bladder decompressed; and FIG. 8 is similar to FIG. 7, but showing the balloon or inflatable bladder inflated such as during use prior to surgery.

DESCRIPTION OF THE PREFERRED EMBODIMENTS

Referring now to the FIGURES, in which identical or similar parts are designated by the same reference numerals throughout and first referring to FIGS. 1-3, a colonic irrigation tube in accordance with the present invention is generally designated by the reference numeral 10. The tube 10 includes an outer tube 12 defining an internal lumen or passageway 14. The external tube 12 preferably has a circular cross-sectional configuration as shown. Another tube 16 defining a smaller lumen or passageway 18 is contained within and runs along the length of the tube 12 along the internal surface thereof. The tube 10 is made of a flexible material, such as polyethylene, polyvinyl or any similar very flexible plastic material, and defines, during use, a distal end 18 received within a colon to be irrigated and an opposing proximal end 20 which is maintained external of the colon.

The tubes 12, 16 define first and second conduit means extending between the proximal and distal ends 20, 18, respectively, the proximal end 16' of the smaller, internal tube 16 being adapted to be connected to a source of irrigation fluid (at 25'), while the proximal end 12' of the larger outer tube 12 is adapted to be connected to a fluid evacuation system (at 25). The specific means or method for connecting the proximal ends of the tubes 12, 16 is not critical for the purposes of the present invention, and any suitable means or method known to those skilled in the art may be used.

The distal ends of the first and second tubes 12, 16 are substantially closed as shown. The smaller, internal tube 16 is provided, however, with outlet or irrigation apertures 22 for discharging fluid from the distal end of the tube 16 into the colon. The apertures may be of any suitable size, but it is presently preferred that such apertures be in the range of 5-7 millimeters in diameter.

The distal end of the larger external tube 12 is provided with inlet or suction apertures 24 for receiving the irrigating fluids as well as fecal material aspirated through the tube 12 during the irrigation procedure.

The distal end of the irrigation tube 10 is enlarged and preferably oval in configuration as shown to facilitate insertion through the rectum, and serving as gripping means for allowing the sensing by the surgeon and gripping thereof through the wall of the colon following insertion therein, to allow the surgeon to pull the irrigation tube into that portion of the colon where irrigation is to be effected or required. Thus, the distal or active end of the colonic irrigation tube 10 can be drawn into the colon any desired distance. The length of the large intestine is typically 4' long in an average adult. The distal end of the colon, however, is usually cleaner and normally need not be irrigated to the extent required for the proximal end of the colon. In a typical application, the length of the colon irrigation tube need not be longer than approximately 3' since with that length all of the areas of the colon normally operated on could be reached and adequately irrigated and aspirated.

While it is not critical for the invention, the irrigating fluid which is typically used is a saline solution which is fed into the inner tube 16 under appropriate pressure.

The width "d" of the outer tube 12 is advantageously 2 centimeters in diameter, although this dimension can be modified somewhat to accommodate the age of the patient since the tube is inserted through the rectum. With a diameter of 2 centimeters for the outer tube 12, the enlarged dimension D or mushroom-shaped tip 26 can typically be approximately 3 centimeters in diameter. The inlet or suction openings or apertures 24 may typically be in the range of from 1-1.2 centimeters in diameter. Such inlet or suction apertures must be sufficiently large to receive the irrigation fluid as well as fecal material which has resulted from the irrigation process.

In operation, referring to FIG. 4, the distal end 18 of the tube 10 is inserted into the colon or large intestine 28 through the rectal opening 30. By sensing the enlarged head 26 through the wall of the colon, the surgeon can draw or pull the irrigation tube 10 into the colon to the extent desired so as to bring the distal end a short distance (e.g. 1-3 inches) from the colonic anastomosis 32. The irrigation process can then commence.

The colonic irrigation tube 10 may also be retained within the colon following surgery to decompress the large intestine. This eliminates the need for nasogastric tubes to aspirate gases created in the stomach by microorganisms as well as gases swallowed by the patient. This application helps to avoid pulmonary infections caused by nasogastric tubes, as well as eliminates the need for sedation of the patient as a result of the use of such gastric tubes. Such gastric tubes have numerous disadvantages, including hampering breathing, causing collapses of the lung and causing discomfort to the patient. By utilizing the colonic irrigation tube, to decompress the large intestine, over distension or blowing-up of the colon is avoided. This protects the anastomosis and helps to prevent contamination and leakage from the anastomosis. Thus, the colon irrigation tube in accordance with the present invention can be efficiently and effectively used both prior to surgery as well as subsequent to surgery of the colon.

Referring to FIGS. 5-8, another embodiment of the invention is shown, wherein the enlarged distal end or head 26 is replaced by an inflatable bladder or balloon 34 which is in the nature of an inflatable annular ring disposed about the distal end of the tube 12. For this purpose, a third tube 36 is used which provides a third passageway or lumen 38 which extends along the length of the tube 12 along the internal surface thereof as shown. The passageway or lumen 38 forms a third conduit which is adapted to be connected to a source of compressed air. Prior to insertion through the rectum 30, the balloon 34 is deflated and, therefore, the maximum width dimension of the tube is substantially equal to the diameter of the tube 12. After the balloon 34 has been received in the colon, air is applied under pressure to the proximal end 36' of the tube 6 to inflate the balloon which, once inflated, serves the same function as the elarged end 26 of the embodiment shown in FIGS. 1-4.

While the invention has been disclosed with respect to specific embodiments, numerous alterations of the structure herein disclosed will be apparent to those ordinarily skilled in the art. The illustrated embodiments are only preferred embodiments of the invention which are given for purposes of illustration only and are not to be construed as a limitation of the invention as set forth in the claims.

What is claimed is:

1. A colon irrigation device comprising a tube made of flexible material and defining, during use, a distal end received within a colon to be irrigated and an opposing proximal end which is maintained external of the colon, said tube further defining first and second conduit means extending between said proximal and distal ends; the proximal end of said first conduit means being connectable to a source of irrigation fluid and the proximal end of said second conduit means being connectable to a fluid evacuation system, the distal ends of said first and second conduit means being substantially closed and having inlet or irrigation aperture means for discharging fluid from the distal end of said first conduit means into the colon and outlet or suction aperture means for receiving the irrigating fluid at the distal end of said second conduit means; and gripping means at the distal end of said tube for allowing sensing and gripping said distal end of said tube through the wall of the colon, said tube having predetermined external dimensions, and said gripping means comprising an enlarged distal end of said tube having dimensions greater than said predetermined external dimensions, said gripping means providing an enlarged surface area within which to increase the sizes or dimensions of said inlet or suction apertures disposed on said gripping means, whereby clogging of said inlet or suction apertures is minimized and said device can be effectively used to provide post-surgery decompression of the colon wherein the dimensions or cross sectional areas of said inlet or suction aperture means are greater than the dimensions or cross sectional areas of said outlet or irrigation aperture means on at least said enlarged distal end.

2. A colon irrigation device as defined in claim 1, wherein said first conduit means comprises a hollow tube having a predetermined diameter and said second conduit means comprises a conduit having a diameter smaller than said predetermined diameter and extending along the inner surface of said hollow tube.

3. A colon irrigation device as defined in claim 1, wherein said first predetermined diameter is approximately 2 cm.

4. A colon irrigation device as defined in claim 1, wherein said inlet or suction aperture means comprises a plurality of aperture openings having diameters in the approximate range of 1-1.2 cm.

5. A colon irrigation device as defined in claim 1, wherein said outlet or irrigation aperture means comprises a plurality of aperture openings having diameters in the range of 5-7 mm.

6. A colon irrigation device as defined in claim 1, wherein said tube has a length equal to approximately 3 feet.

7. A colon irrigation device as defined in claim 1, wherein said enlarged distal end is provided with said outlet aperture means.

8. A colon irrigation device as defined in claim 1, wherein said inlet or suction aperture means has dimensions or cross sectional areas on the order of magnitude of said predetermined external dimensions of said tube.

9. A colon irrigation device comprising a tube made of flexible material and defining, during use, a distal end received within a colon to be irrigated and an opposing proximal end which is maintained external of the colon, said tube further defining first and second conduit means extending between said proximal and distal ends; the proximal end of said first conduit means being connectable to a source of irrigation fluid and the proximal end of said second conduit means being connectable to a fluid evacuation system, the distal ends of said first and second conduit means being substantially closed and having inlet or irrigation aperture means for discharging fluid from the distal end of said first conduit means into the colon and outlet or suction aperture means for receiving the irrigating fluid at the distal end of said second conduit means; gripping means at the distal end of said tube for allowing sensing and gripping said distal end of said tube through the wall of the colon, said tube having predetermined external dimensions, and said gripping means comprising an enlarged distal end of said tube having dimensions greater than said predetermined external dimensions, said gripping means providing an enlarged surface area within which to increase the sizes or dimensions of said inlet or suction apertures disposed on said gripping means, whereby clogging of said inlet or suction apertures is minimized and said device can be effectively used to provide post-surgery decompression of the colon; and third conduit means extending between said distal and proximal ends, said gripping means comprising an inflatable annular ring extending about said tube and in fluid flow communication with said fluid conduit means whereby said inflatable annular ring can be inflated following insertion into the colon to allow sensing and gripping thereof.

* * * * *